United States Patent
Jang et al.

(10) Patent No.: US 11,648,068 B2
(45) Date of Patent: May 16, 2023

(54) MAGNETIC ROBOT SYSTEM

(71) Applicant: IUCF-HYU (INDUSTRY-UNIVERSITY COOPERATION FOUNDATION HANYANG UNIVERSITY), Seoul (KR)

(72) Inventors: Gunhee Jang, Seoul (KR); Wonseo Lee, Yongin-si (KR); Jae Kwang Nam, Goyang-si (KR); Jongyul Kim, Gimhae-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 622 days.

(21) Appl. No.: 16/637,472

(22) PCT Filed: Apr. 3, 2018

(86) PCT No.: PCT/KR2018/003910
§ 371 (c)(1),
(2) Date: Feb. 7, 2020

(87) PCT Pub. No.: WO2019/031678
PCT Pub. Date: Feb. 14, 2019

(65) Prior Publication Data
US 2020/0246087 A1    Aug. 6, 2020

(30) Foreign Application Priority Data
Aug. 11, 2017 (KR) .................. 10-2017-0102073

(51) Int. Cl.
*A61B 17/3207* (2006.01)
*A61B 17/00* (2006.01)
(Continued)

(52) U.S. Cl.
CPC .............. *A61B 34/30* (2016.02); *A61B 34/70* (2016.02); *A61B 2017/00292* (2013.01);
(Continued)

(58) Field of Classification Search
CPC .................... A61B 34/30; A61B 34/70; A61B 2017/00292; A61B 2017/00314;
(Continued)

(56) References Cited

U.S. PATENT DOCUMENTS

2007/0161862 A1    7/2007  Yokoi et al.
2008/0269871 A1*  10/2008  Eli ........................ A61F 2/0108
                                                                         623/1.42
(Continued)

FOREIGN PATENT DOCUMENTS

CN          101743157 A       6/2010
KR    10-2008-0009988 A       1/2008
(Continued)

OTHER PUBLICATIONS

International Search Report of PCT/KR2018/003910 dated Jul. 16, 2018, 4 pages.

*Primary Examiner* — Timothy J Neal
*Assistant Examiner* — Andrew P. Restaino (57) ABSTRACT

A magnetic robot system is provided. The magnetic robot system comprises: a catheter having a first magnet coupling part provided at the front end thereof; and a mobile robot having a second magnet coupling part provided at the rear end thereof, and having a driving magnet, wherein the mobile robot is coupled to the catheter by means of magnetic force between the first magnet coupling part and the second magnet coupling part, and the magnetic force coupling of the first magnet coupling part and the second magnet coupling
(Continued)

part can be released by rotating magnetic torque generated by the driving magnet because of the application of external rotating magnetic force.

10 Claims, 4 Drawing Sheets

(51) Int. Cl.
*A61B 34/30* (2016.01)
*A61B 34/00* (2016.01)

(52) U.S. Cl.
CPC ............ *A61B 2017/00314* (2013.01); *A61B 2017/00473* (2013.01); *A61B 2017/00477* (2013.01); *A61B 2017/00876* (2013.01); *A61B 2017/320733* (2013.01); *A61B 2017/320775* (2013.01); *A61B 2034/301* (2016.02)

(58) Field of Classification Search
CPC ........... A61B 2017/00473; A61B 2017/00477; A61B 2017/00876; A61B 2017/320733; A61B 2017/320775; A61B 2034/301; A61B 2017/00345; A61B 2017/00469; A61B 34/73; A61B 2034/303; A61B 2034/731; B25J 9/065
See application file for complete search history.

(56) References Cited

U.S. PATENT DOCUMENTS

| | | | |
|---|---|---|---|
| 2010/0145143 A1 | 6/2010 | Salomon et al. | |
| 2011/0282337 A1* | 11/2011 | Hall | A61B 10/0266 606/171 |
| 2016/0235491 A1 | 8/2016 | Choi et al. | |

FOREIGN PATENT DOCUMENTS

| | | |
|---|---|---|
| KR | 10-2008-0079037 A | 8/2008 |
| KR | 10-2010-0012394 A | 2/2010 |
| KR | 10-2014-0026957 A | 3/2014 |
| KR | 10-1379859 B1 | 4/2014 |
| KR | 10-1394798 B1 | 5/2014 |
| KR | 10-1543708 B1 | 8/2015 |
| KR | 10-1659367 B1 | 9/2016 |
| KR | 10-1749586 B1 | 6/2017 |
| WO | 2009145405 A1 | 12/2009 |

* cited by examiner

MAGNETIC ROBOT SYSTEM

CROSS REFERENCE TO RELATED APPLICATIONS

This application is a National Stage of International Application No. PCT/KR2018/003910 filed Apr. 3, 2018, claiming priority based on Korean Patent Application No. 10-2017-0102073 filed Aug. 11, 2017.

TECHNICAL FIELD

The present invention relates to a magnetic robot system, and more particularly, to a magnetic robot system capable of effectively transporting and recovering a mobile robot to and from a point close to a lesion site in a vessel such as a blood vessel.

BACKGROUND ART

In order to treat vascular diseases in areas that are blocked or narrowed due to a thrombus or the like, coronary angioplasty is generally performed in an order of inserting a catheter through a femoral artery, expanding a blood vessel by a manual operation of a doctor, and installing a device for maintaining the expanded blood vessel. However, due to structural characteristics of the catheter, it is difficult to apply the catheter to complex blood vessels, and success of a medical procedure largely depends on a level of proficiency of the doctor.

Recently, in order to overcome such disadvantages of the catheter, researches on a magnetic robot for vascular therapy that can be wirelessly driven have been actively conducted. However, most of magnetic robots that have been developed up to the present time are provided in a unit of a single module, and mainly move by floating without making contact with a wall in a vessel or by using a frictional force generated by making contact with the wall in the vessel. In an environment where a diameter of the vessel changes or a pulsatile flow occurs, an environment where the vessel moves, or the like, there are limitations in maintaining a position and a posture of the magnetic robot as well as in smoothly operating the magnetic robot.

In addition, researches on a method of stably moving the wirelessly-driven magnetic robot to a periphery of a lesion in a human body and recovering the magnetic robot after a treatment are insufficient.

DISCLOSURE

Technical Problem

A technical object of the present invention is to provide a magnetic robot system capable of effectively transporting and recovering a mobile robot to and from a point close to a lesion site in a vessel such as a blood vessel (B.V).

The technical objects of the present invention are not limited to the above-described objects.

Technical Solution

A magnetic robot system includes: a catheter provided at a front end thereof with a first magnet coupling part; and a mobile robot provided at a rear end thereof with a second magnet coupling part and having a driving magnet, wherein the mobile robot is coupled to the catheter by a magnetic force between the first magnet coupling part and the second magnet coupling part, and a magnetic coupling between the first magnet coupling part and the second magnet coupling part is released by a rotating magnetic torque which is generated in the driving magnet as an external rotating magnetic force is applied.

In addition, the first magnet coupling part may include: a first magnet layer having a plate shape; and a second magnet layer having a plate shape and stacked on the first magnet layer such that opposite polarities face each other between the first and second magnet layers.

In addition, an area of polarity of the first magnet layer may be equal to an area of polarity of the second magnet layer.

In addition, the second magnet coupling part may include: a third magnet layer having a plate shape; and a fourth magnet layer having a plate shape and stacked on the third magnet layer such that opposite polarities face each other between the third and fourth magnet layers.

In addition, an area of polarity of the third magnet layer may be equal to an area of polarity of the fourth magnet layer.

In addition, the magnetic robot system may further include a spacer coupled to a front end of the first magnet coupling part and formed of a nonmagnetic material, wherein the spacer may be located between the first magnet coupling part and the second magnet coupling part when the mobile robot is coupled to the catheter.

In addition, the mobile robot may include: a mobile robot body part to which the driving magnet is coupled; and a plurality of blades formed of a flexible material, provided along a circumference of the mobile robot body part, and coupled to the mobile robot body part in an oblique direction with respect to a rotation axis of the driving magnet.

In addition, a plurality of mobile robot body parts may be arranged in series, and the mobile robot may further include flexible coupling parts provided between the mobile robot body parts and connected to adjacent mobile robot body parts, respectively.

Advantageous Effects

According to the present invention, the catheter and the mobile robot are coupled to each other by a magnetic field, so that the mobile robot can be easily transported to the lesion site in the human body, and the mobile robot can be recovered.

In addition, according to the present invention, the catheter can be used to safely and effectively transport the mobile robot in an environment filled with a fluid, such as a blood vessel (B.V).

BEST MODE

A magnetic robot system according to the present invention includes: a catheter provided at a front end thereof with a first magnet coupling part; and a mobile robot provided at a rear end thereof with a second magnet coupling part and having a driving magnet, wherein the mobile robot is coupled to the catheter by a magnetic force between the first magnet coupling part and the second magnet coupling part, and a magnetic coupling between the first magnet coupling part and the second magnet coupling part is released by a rotating magnetic torque which is generated in the driving magnet as an external rotating magnetic force is applied.

Mode for Invention

Hereinafter, exemplary embodiments of the present invention will be described in detail with reference to the accompanying drawings. However, the technical idea of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the present disclosure that one element is on another element, it means that a first element may be directly formed on a second element, or a third element may be interposed between the first element and the second element. Further, in the drawings, thicknesses of membranes and areas are exaggerated for efficient description of the technical contents.

In addition, in the various embodiments of the present disclosure, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments described and illustrated herein include their complementary embodiments. Further, the term "and/or" in the present disclosure is used to include at least one of the elements enumerated before and after the term.

In the present disclosure, the terms of a singular form may include plural forms unless the context clearly indicates otherwise. Further, the terms such as "including" and "having" are used to designate the presence of features, numbers, steps, elements, or combinations thereof described in the present disclosure, and shall not be construed to preclude any possibility of presence or addition of one or more other features, numbers, steps, elements, or combinations thereof. In addition, the term "connection" in the present disclosure may be used to include both indirectly and directly connecting a plurality of elements.

Further, in the following description of the present invention, a detailed description of known functions and configurations incorporated herein will be omitted when it may make the subject matter of the present invention unnecessarily unclear.

Figure 1:
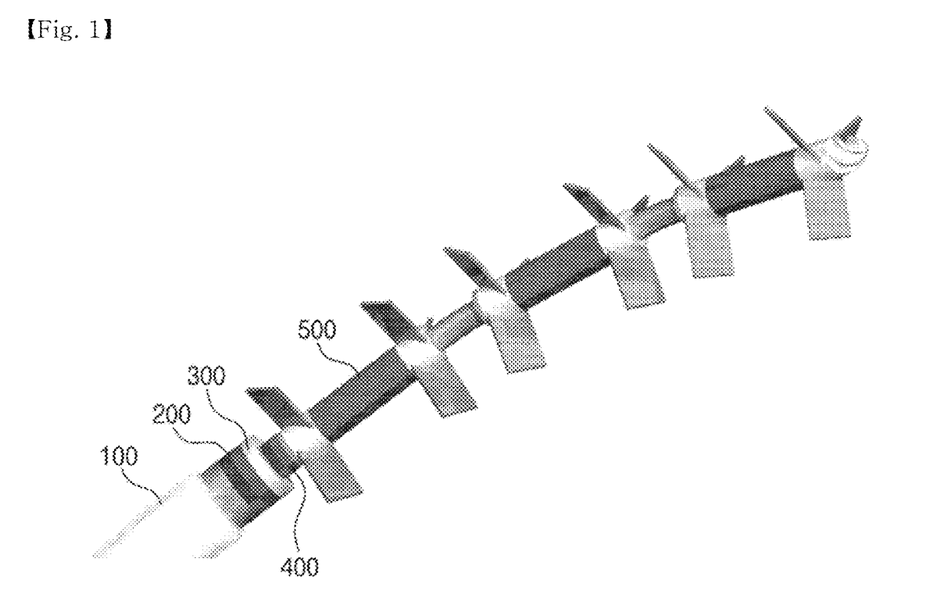
FIG. 1 is a perspective view showing a magnetic robot system according to one embodiment of the present invention.
Figure 2:
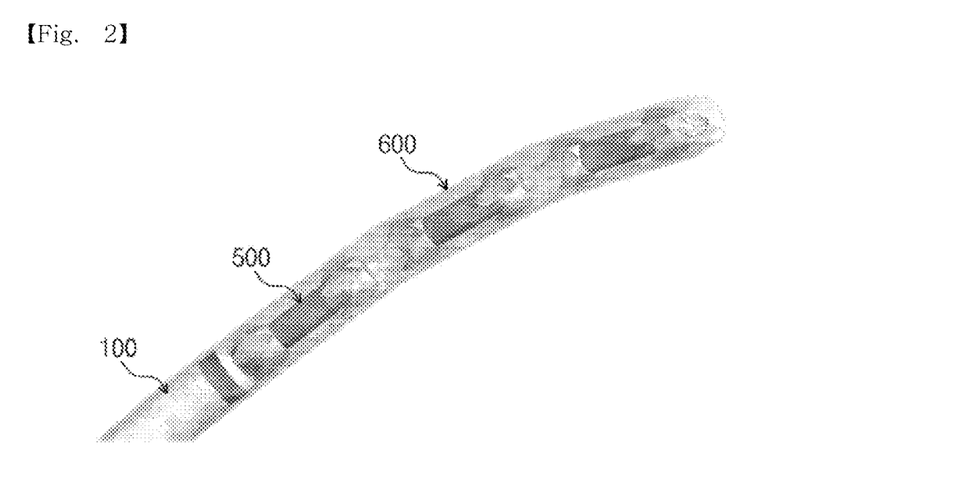
FIG. 2 is a perspective view showing the magnetic robot system according to one embodiment of the present invention.

FIGS. 1 and 2 are perspective views showing a magnetic robot system according to one embodiment of the present invention.

Referring to FIGS. 1 and 2, the magnetic robot system may insert and transport a mobile robot 500, which is coupled to a catheter 100, into a human body. In particular, the magnetic robot system may insert the mobile robot 500 into tubular tissues such as body cavities in the human body (pleural cavity and peritoneal cavity) and tubular organs (bronchus, esophagus, stomach, intestine, urinary bladder, ureter, and blood vessels (B.V)) to transport the mobile robot 500 to a region close to a lesion.

The magnetic robot system may include a catheter 100, a first magnet coupling part 200, a spacer 300, a second magnet coupling part 400, a mobile robot 500, and a tube 600. The catheter 100, the first magnet coupling part 200, the spacer 300, the second magnet coupling part 400, and the mobile robot 500 may be sequentially coupled to each other in one direction.

Figure 3:
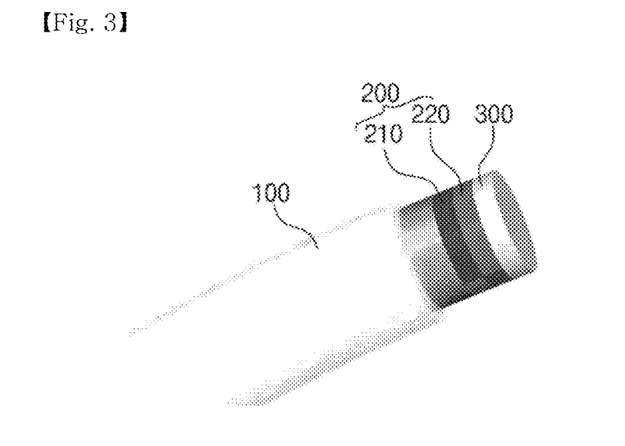
FIG. 3 is a perspective view showing a catheter, a first magnet coupling part, and a spacer according to one embodiment of the present invention.

FIG. 3 is a perspective view showing a catheter 100, a first magnet coupling part 200, and a spacer 300 according to one embodiment of the present invention.

Referring to FIGS. 1 and 3, the catheter 100 may be provided at a front end thereof with a first magnet coupling part 200. In addition, the first magnet coupling part 200 may be at a front end thereof with the spacer 300.

The first magnet coupling part 200 may include a first magnet layer 210 and a second magnet layer 220. The first magnet layer 210 and the second magnet layer 220 may be permanent magnets having a plate shape and bisected into an N-pole and an S-pole. The second magnet layer 220 may be stacked on the first magnet layer 210, and may be provided such that opposite polarities face each other between the first and second magnet layers 210 and 220.

An area of polarity of the first magnet layer 210 may be equal to an area of polarity of the second magnet layer 220. Since the first magnet layer 210 and the second magnet layer 220 are arranged such that N-poles and S-poles, which are the opposite polarities having the same intensity, face each other, a value of a total magnetic moment may become zero, so that the first magnet layer 210 and the second magnet layer 220 may not be affected by an external rotating magnetic field. In other words, when the external rotating magnetic force is applied, a rotation torque may not be generated by the external rotating magnetic force.

The spacer 300 may be provided between the front end of the first magnet coupling part 200 and a rear end of the second magnet coupling part 400. The spacer 300 may block the first magnet coupling part 200 and the second magnet coupling part 400 from being directly coupled to each other by a magnetic force. The spacer 300 may have a plate shape having a predetermined thickness, and may have a radius corresponding to or greater than a radius of the first magnet coupling part 200 or the second magnet coupling part 400. The spacer 300 may maintain a distance between the first magnet coupling part 200 and the second magnet coupling part 400 at a predetermined interval when the first magnet coupling part 200 and the second magnet coupling part 400 are coupled to each other by the magnetic force. The spacer 300 may be formed of a nonmagnetic material. Therefore, the spacer 300 may not exert a magnetic force on the first and second magnet coupling parts 200 and 400. The thickness of the spacer 300 may vary depending on a design, so that the spacer 300 may adjust a magnitude of the magnetic force between the first magnet coupling part 200 and the second magnet coupling part 400. In addition, the spacer 300 may facilitate separation between the first magnet coupling part 200 and the second magnet coupling part 400.

The spacer 300 may be fixedly coupled to one of the front end of the first magnet coupling part 200 and the rear end of the second magnet coupling part 400. According to the embodiment, the spacer 30 may be fixedly coupled to the front end of the first magnet coupling part 200. The spacer 300 may be fixedly coupled to the front end of the first magnet coupling part 200 by a coupling device other than the magnetic force, for example, an adhesive or a mechanical coupling device.

Figure 4:
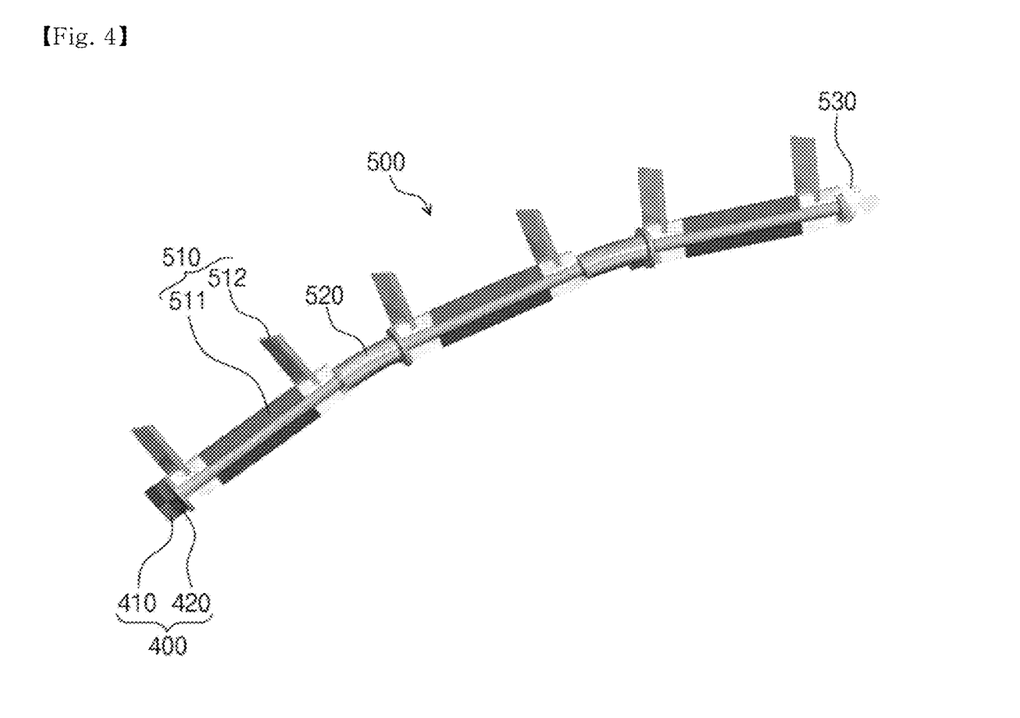
FIG. 4 is a perspective view showing a second magnet coupling part and a mobile robot according to one embodiment of the present invention.

FIG. 4 is a perspective view showing a second magnet coupling part 400 and a mobile robot 500 according to one embodiment of the present invention.

Referring to FIGS. 1 and 4, the second magnet coupling part 400 may be provided at a rear end of the mobile robot 500. The second magnet coupling part 400 and the first magnet coupling part 200 may exert a magnetic force on each other only when the second magnet coupling part 400 approaches the first magnet coupling part 200 within a predetermined distance. The second magnet coupling part 400 may couple the mobile robot 500 to the catheter 100 by the magnetic force with the first magnet coupling part 200.

The second magnet coupling part 400 may include a third magnet layer 410 and a fourth magnet layer 420. The third magnet layer 410 and the fourth magnet layer 420 may be permanent magnets having a plate shape and bisected into an N-pole and an S-pole. The fourth magnet layer 420 may be stacked on the third magnet layer 410, and may be provided such that opposite polarities face each other between the third and fourth magnet layers 410 and 220.

An area of polarity of the third magnet layer 410 may be equal to an area of polarity of the fourth magnet layer 420. Since the third magnet layer 410 and the fourth magnet layer 420 are arranged such that N-poles and S-poles, which are the opposite polarities having the same intensity, face each other, a value of a total magnetic moment may become zero, so that the third magnet layer 410 and the fourth magnet layer 420 may not be affected by an external rotating magnetic field. In other words, a rotation torque may not be generated by the external rotating magnetic force.

The mobile robot 500 may include a mobile robot body part 510, a driving magnet 511, a blade 512, a flexible coupling part 520, and a drill tip 530.

A plurality of mobile robot body parts 510 may be coupled to each other in series. The mobile robot body part 510 may be formed of a rigid material, and may have a predetermined length.

The driving magnet 511 may have a cylindrical shape, and may be bisected into an N-pole and an S-pole about a central axis thereof. The driving magnet 511 may surround a circumference of the mobile robot body part 510, and the central axis of the driving magnet 511 may be provided on the same axis as a rotation axis of the mobile robot body part 510.

The flexible coupling part 520 may connect the mobile robot body parts 510 to each other. The flexible coupling part 520 may be formed of a flexible material to change a shape of the mobile robot 500 according to an intravascular environment.

A plurality of blades 512 may be provided along the circumference of the mobile robot body part 510. According to the embodiment, the blades 512 may be provided at front and rear ends of the mobile robot body part 510, respectively. The blades 512 may be arranged in an oblique direction with respect to a rotation axis of the driving magnet 511. The blade 512 may be formed of a flexible material so that a shape of the blade 512 may be changed according to a structural environment in a vessel. The blade 512 may generate a propulsive force like a propeller when the mobile robot 500 rotates.

The drill tip 530 may be provided at the front end of the mobile robot 500. In detail, the drip tip 530 may be provided at a front end of a mobile robot body part 510 which is located at a foremost end of the plurality of mobile robot body parts 510. The drill tip 530 may perform a drilling operation to widen a passage in a constricted-tube environment when the mobile robot body part 510 is rotated by the external rotating magnetic field.

Referring again to FIG. 2, the tube 600 may surround an entirety of the catheter 100 and the mobile robot 500, and may facilitate entry and transport of the catheter 100 and the mobile robot 500 in an environment inside a vessel such as a blood vessel (B.V). The tube 600 may be formed of a flexible material.

Figure 6:
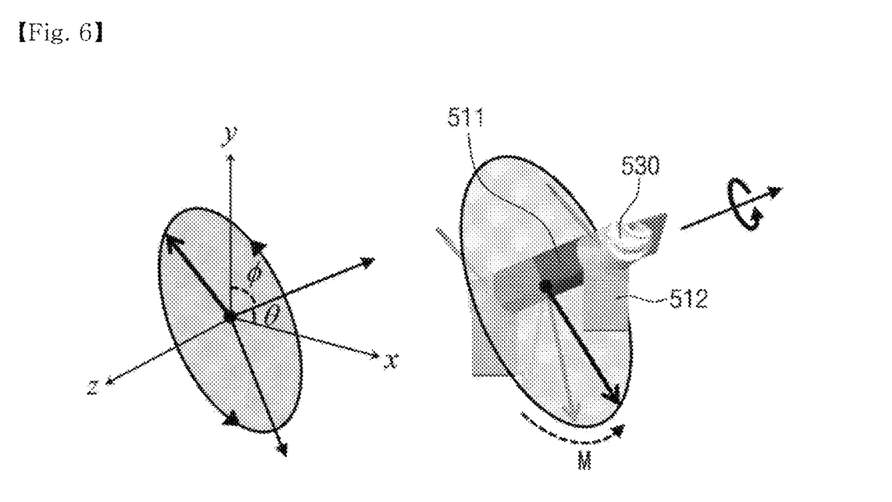
FIG. 6 is a view for describing a rotation state of the mobile robot caused by an external rotating magnetic field according to one embodiment of the present invention.

FIG. 6 is a view for describing a rotation state of the mobile robot 500 caused by an external rotating magnetic field according to one embodiment of the present invention.

Referring to FIG. 6, the driving magnet 511 may control an operation of the mobile robot 500 by a rotating magnetic field applied from an outside. In other words, when the external rotating magnetic field is generated, the mobile robot body part 510 may rotate about a central axis thereof by a magnetic torque generated in the driving magnet 511.

In this case, the magnetic torque exerted on the driving magnet 511 may be calculated through Mathematical formulas 1 and 2 below.

When the external magnetic field is applied, the magnetic torque exerted on the driving magnet 511 may be defined by Mathematical formula 1 below.

$$\vec{T} = \vec{m} \times \vec{B}$$ [Mathematical formula 1]

(T is the magnetic torque exerted on the driving magnet 511, m is a magnetic moment of the driving magnet 511, and B is the external magnetic field)

Due to Mathematical formula 1, the external rotating magnetic field for generating a rotational motion of the mobile robot 500 may be defined by Mathematical formula 2 below.

$$\vec{B} = B_0(\cos 2\pi ft U + \sin 2\pi ft N \times U)$$ [Mathematical formula 2]

($B_0$ is intensity of the external rotating magnetic field, f is a frequency of the external rotating magnetic field, t is a time, N is a rotation axis vector of the magnetic robot, and U is a rotation axis vector perpendicular to N)

In this case, the driving magnet 511 may generate the rotational motion according to a direction of the external rotating magnetic field M, and the mobile robot 500 may move by using the propulsive force generated by the blade 512.

Hereinafter, a method of transporting the mobile robot 500 to a lesion site in the vessel, separating the mobile robot 500, and recovering the mobile robot 500 after driving the mobile robot 500 by using the above-described magnetic robot system will be described.

Referring again to FIGS. 1 and 2, when the micro-robot system is transported to a point close to the lesion site, the magnetic robot system may be transported while the catheter 100 and the mobile robot 500 are coupled to each other in series and wrapped inside the tube 600. In this case, the catheter 100 may be coupled to the mobile robot 500 by a magnetic force between the first magnet coupling part 200 and the second magnet coupling part 400 which have the spacer 300 interposed therebetween.

The magnetic robot system may be stably transported while being surrounded by the tube 600 formed of a flexible material that may be deformed according to the environment of the vessel such as a blood vessel (B.V). At this time, the blade 512 may be changed to a shape suitable for an inner diameter of the tube 600. In this case, the mobile robot 500 may have a predetermined level of steering capability by applying the external magnetic field to exert the magnetic torque on the driving magnet 511.

When the magnetic robot system reaches a portion in the vicinity of the lesion site, the tube 600 surrounding the catheter 100, the first magnet coupling part 200, the spacer 300, the second magnet coupling part 400, and the mobile robot 500 may be separated by an operation of an operator.

Figure 5:
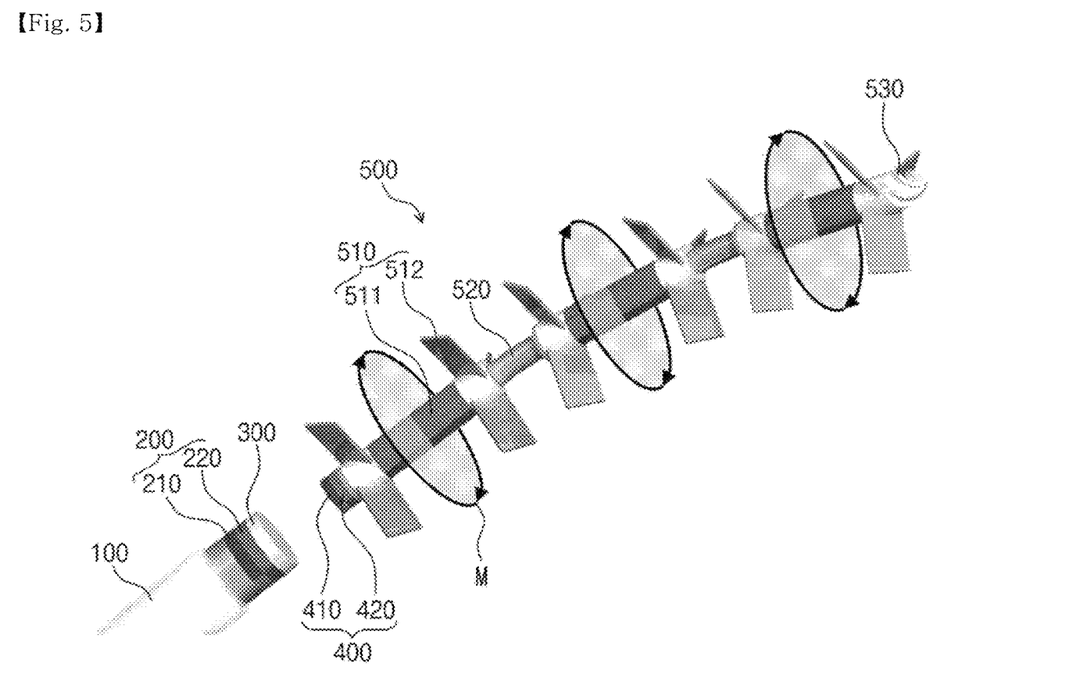
FIG. 5 is a view for describing a process of separating the mobile robot from the catheter according to one embodiment of the present invention.

FIG. 5 is a view for describing a process of separating the mobile robot from the catheter according to one embodiment of the present invention.

Referring to FIG. 5, when the external rotating magnetic field is applied, the magnetic torque may be exerted on the driving magnet 511 of each of the mobile robot body parts 510 to rotate the driving magnet 511. Due to a propulsive force generated at this time, the magnetic force between the first magnet coupling part 200 and the second magnet coupling part 400 may be canceled, so that the mobile robot 500 may be separated from the catheter 100. The separated mobile robot 500 may be individually controlled and moved by the external rotating magnetic field.

In detail, when a rotational frequency of the external rotating magnetic field is applied to a predetermined level or more, a propulsive force having a sufficient magnitude may be generated in the mobile robot 500. The generated propulsive force may overcome the magnetic force between the first magnet coupling part 200 and the second magnet coupling part 400, so that a coupling between the first magnet coupling part 200 and the second magnet coupling part 400 may be separated. In this case, the spacer 300 may facilitate the separation of the first magnet coupling part 200 and the second magnet coupling part 400.

Figure 7:
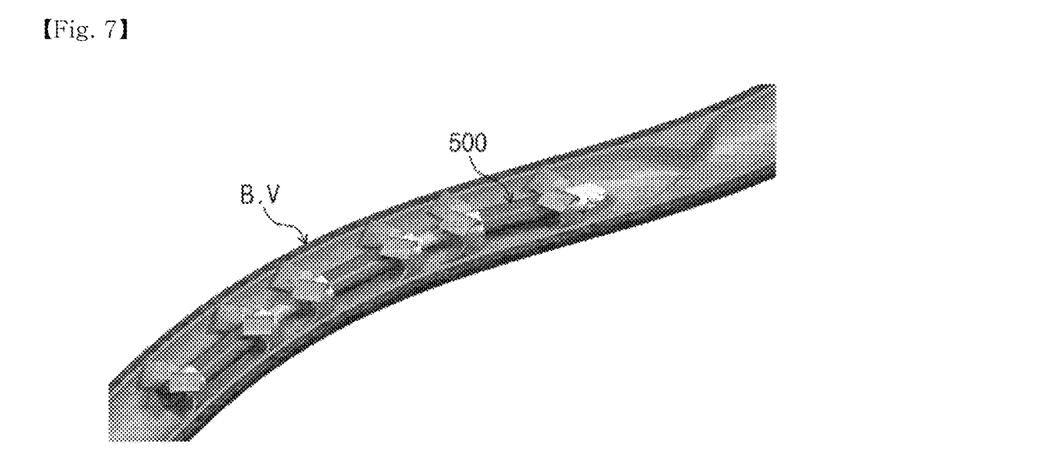
FIG. 7 is a view showing an operating state of the mobile robot in an intravascular environment according to one embodiment of the present invention.

FIG. 7 is a view showing an operating state of the mobile robot 500 in an intravascular environment according to one embodiment of the present invention.

Referring to FIG. 7, a rotational plane of the external rotating magnetic field may be controlled so as to be applied perpendicularly to an axial direction of the mobile robot 500, and the mobile robot body parts 510 may stably rotate and generate a propulsive force as the magnetic torque is generated.

Referring again to FIG. 5, when the driving of the mobile robot 500 is completed, the mobile robot 500 may be recovered.

When the mobile robot 500 is recovered, the first magnet coupling part 200 may be controlled to approach the second magnet coupling part 400 by using the catheter 100. The mobile robot 500 may be coupled to the catheter 100 due to the magnetic force generated between the first magnet coupling part 200 and the second magnet coupling part 400.

Then, after the catheter 100 and the mobile robot 500 are wrapped with the tube 600, the magnetic robot system may be recovered to the outside of the human body.

Although the exemplary embodiments of the present invention have been described in detail, the scope of the present invention is not limited to a specific embodiment, and should be interpreted by the appended claims. In addition, it should be understood by those skilled in the art to which the invention pertains that various changes and modifications can be made without departing from the scope of the present invention.

INDUSTRIAL APPLICABILITY

The present invention may be applied to the transport and recovery of a mobile robot in tubular tissues of a human body, such as blood vessels, digestive organs, and urethra.

The invention claimed is:

1. A magnetic robot system comprising:
   a mobile robot body part;
   a driving magnet fixedly coupled to the mobile robot body part and generating a rotating magnetic torque upon application of an external rotating magnetic force; and
   a plurality of plate-shaped blades formed of a flexible material, and provided along a circumference of the mobile robot body part and coupled to the mobile robot body part in a direction that is arranged in an oblique direction with respect to a rotational axis of the driving magnet,
   wherein the plurality of blades are arranged radially about the rotational axis of the driving magnet, and one end of each blade of the plurality of blades is engaged with the outer circumferential surface of the mobile robot body part.

2. The magnetic robot system of claim 1, comprising:
   a drill tip coupled to a distal end of the mobile robot body part.

3. The magnetic robot system of claim 1, wherein the mobile robot body part is provided in plural,
   the mobile robot body parts are coupled to each in series, and wherein the magnetic robot system further includes:
   a flexible coupling part provided between the mobile robot body parts and connecting the mobile robot body parts to each other.

4. The magnetic robot system of claim 1, further comprising:
   a catheter;
   a first magnet coupling part coupled to a front end of the catheter; and
   a second magnet coupling part coupled to a rear end of the mobile robot body part,
   wherein the mobile robot body part is coupled to the catheter by a magnetic coupling force between the first magnet coupling part and the second magnet coupling part, and
   a magnetic coupling between the first magnet coupling part and the second magnet coupling part is configured to be released by the rotating magnetic torque.

5. The magnetic robot system of claim 4, wherein the first magnet coupling part comprises:
   a first magnet layer having a plate shape, and coupled to the front end of the catheter; and
   a second magnet layer having a plate shape, and stacked on the first magnet layer and provided such that polarities of the second magnet layer face the opposite polarities of the first magnet layer.

6. The magnetic robot system of claim 5, wherein the first magnet layer has the same polarity area as the second magnet layer.

7. The magnetic robot system of claim 5, wherein the second magnet coupling part includes:
   a third magnet layer having a plate shape; and
   a fourth magnet layer having a plate shape and stacked on the third magnet layer such that opposite polarities face each other between the third and fourth magnet layers.

8. The magnetic robot system of claim 7, wherein an area of polarity of the third magnet layer is equal to an area of polarity of the fourth magnet layer.

9. The magnetic robot system of claim 4, further comprising a spacer coupled to a front end of the first magnet coupling part and formed of a nonmagnetic material,
   wherein the spacer is located between the first magnet coupling part and the second magnet coupling part when the mobile robot is coupled to the catheter.

10. The magnetic robot system of claim 4, further comprising a tube formed of a flexible material and configured to surround outer sides of the catheter, the first magnet coupling part, the second magnet coupling part, and the mobile robot.

\* \* \* \* \*